(12) United States Patent
Kang et al.

(10) Patent No.: US 12,324,689 B2
(45) Date of Patent: Jun. 10, 2025

(54) METHOD FOR GENERATING ALARM ABOUT CONTINUOUS BIOMETRIC INFORMATION

(71) Applicant: I-SENS, INC., Seoul (KR)

(72) Inventors: Young Jae Kang, Seoul (KR); Jeong Je Park, Seoul (KR); Seung Chun Lee, Seoul (KR)

(73) Assignee: I-SENS, INC., Seoul (KR)

( * ) Notice: Subject to any disclaimer, the term of this patent is extended or adjusted under 35 U.S.C. 154(b) by 0 days.

(21) Appl. No.: 18/396,707

(22) Filed: Dec. 27, 2023

(65) Prior Publication Data

US 2024/0122554 A1    Apr. 18, 2024

Related U.S. Application Data

(63) Continuation of application No. 18/265,432, filed as application No. PCT/KR2021/008924 on Jul. 13, 2021.

(30) Foreign Application Priority Data

Dec. 14, 2020   (KR) .......................... 10-2020-0174276

(51) Int. Cl.
*A61B 5/00*   (2006.01)
*A61B 5/145*   (2006.01)
(Continued)

(52) U.S. Cl.
CPC .......... *A61B 5/746* (2013.01); *A61B 5/14532* (2013.01); *A61B 5/1495* (2013.01); *A61B 5/748* (2013.01); *G08B 29/20* (2013.01)

(58) Field of Classification Search
CPC ... A61B 5/746; A61B 5/14532; A61B 5/1495; A61B 5/748; G08B 29/20
See application file for complete search history.

(56) References Cited

U.S. PATENT DOCUMENTS 8,803,688 B2 *   8/2014   Halff ................... G16H 40/67
                                                   604/890.1
10,080,529 B2 *   9/2018   Fox .................... A61B 5/14532
(Continued)

FOREIGN PATENT DOCUMENTS

CN            107453779       12/2017
JP            2004005341 A *   1/2004
(Continued)

OTHER PUBLICATIONS

Extended European Search Report dated Mar. 15, 2024 for European Patent Application No. 21906772.5.
(Continued)

*Primary Examiner* — Chico A Foxx
(74) *Attorney, Agent, or Firm* — WOMBLE BOND DICKINSON (US)

(57) ABSTRACT

The present invention relates to a method for generating an alarm pertaining to continuous biometric data and, more specifically, to an alarm generation method in which, if an alarm condition is satisfied, an alarm is output to a user while maintaining the alarm in an activated state during a set alarm period, and changing the alarm type selected by the user during the alarm period, thereby enabling the user to be prompted to input information or take an action in response to the alarm without ignoring the alarm, while not causing inconvenience to the user due to frequent alarms; and when the alarm condition is satisfied, an operating mode of a receiver is determined and the alarm type, which has been set in accordance with the alarm condition, is changed to an alarm type corresponding to the operating mode of the receiver, thereby making it possible to prevent an alarm from being generated against the user's wishes.

9 Claims, 7 Drawing Sheets

(51) Int. Cl.
*A61B 5/1495* (2006.01)
*G08B 29/20* (2006.01)

(56) References Cited

U.S. PATENT DOCUMENTS

| | | | | |
|---|---|---|---|---|
| 10,499,811 | B2* | 12/2019 | Mensinger | A61B 5/7264 |
| 2001/0040509 | A1* | 11/2001 | Dungan | G01N 33/0075 |
| | | | | 340/634 |
| 2005/0027182 | A1* | 2/2005 | Siddiqui | G16H 15/00 |
| | | | | 128/903 |
| 2005/0038332 | A1* | 2/2005 | Saidara | G16H 40/67 |
| | | | | 128/920 |
| 2008/0079595 | A1* | 4/2008 | Baier | G05B 23/0235 |
| | | | | 340/506 |
| 2008/0319284 | A1* | 12/2008 | Alvarez-Icaza | G09B 23/12 |
| | | | | 600/309 |
| 2011/0118573 | A1* | 5/2011 | McKenna | A61B 5/746 |
| | | | | 600/323 |
| 2011/0118578 | A1* | 5/2011 | Timmerman | A61B 5/4839 |
| | | | | 604/890.1 |
| 2011/0201911 | A1 | 8/2011 | Johnson et al. | |
| 2012/0277723 | A1* | 11/2012 | Skladnev | A61M 5/1723 |
| | | | | 604/504 |
| 2012/0293323 | A1 | 11/2012 | Kaib et al. | |
| 2014/0012511 | A1* | 1/2014 | Mensinger | A61B 5/4839 |
| | | | | 702/19 |
| 2014/0118166 | A1* | 5/2014 | Hampapuram | A61B 5/746 |
| | | | | 340/870.16 |
| 2014/0278229 | A1* | 9/2014 | Hong | H04W 4/027 |
| | | | | 702/160 |
| 2015/0351695 | A1* | 12/2015 | Cronin | A61B 5/7475 |
| | | | | 600/300 |
| 2016/0066867 | A1* | 3/2016 | Mensinger | A61B 5/742 |
| | | | | 340/539.12 |
| 2016/0270740 | A1* | 9/2016 | Raisoni | A61B 5/14532 |
| 2016/0302741 | A1* | 10/2016 | Miyamura | A61B 5/742 |
| 2017/0186305 | A1 | 6/2017 | Marc | |
| 2017/0286194 | A1 | 10/2017 | Morris et al. | |
| 2018/0049649 | A1* | 2/2018 | Addison | A61B 5/14546 |
| 2018/0315285 | A1 | 11/2018 | Janssen | |
| 2019/0274624 | A1 | 9/2019 | Mazlish et al. | |
| 2020/0090508 | A1* | 3/2020 | Baker | G08G 1/081 |
| 2020/0305772 | A1 | 10/2020 | Oh et al. | |
| 2021/0085225 | A1 | 3/2021 | Park et al. | |
| 2021/0391050 | A1* | 12/2021 | Wiktorowicz | G16H 40/67 |
| 2022/0142524 | A1* | 5/2022 | Harper | A61B 5/7445 |
| 2022/0218292 | A1* | 7/2022 | Crowley | G16H 10/20 |
| 2022/0240819 | A1* | 8/2022 | Lee | G16H 10/60 |
| 2022/0248988 | A1* | 8/2022 | Kumar | A61B 5/746 |
| 2023/0200753 | A1* | 6/2023 | McGarraugh | A61B 5/746 |
| | | | | 600/347 |
| 2024/0173475 | A1* | 5/2024 | Rosinko | A61B 5/7405 |

FOREIGN PATENT DOCUMENTS

| | | | | |
|---|---|---|---|---|
| JP | 2015-511500 | | 4/2015 | |
| JP | 2020-151110 | | 9/2020 | |
| JP | 2020151110 | A * | 9/2020 | |
| JP | 2020-185365 | | 11/2020 | |
| KR | 10-2006-0127678 | | 12/2006 | |
| KR | 20060127678 | A * | 12/2006 | |
| KR | 10-2009-0038647 | | 4/2009 | |
| KR | 10-2019-0057759 | | 5/2019 | |
| KR | 10-2019-0098444 | | 8/2019 | |
| WO | WO-2008072842 | A1 * | 6/2008 | A63B 69/0059 |
| WO | WO-2013129924 | A2 * | 9/2013 | A61B 5/1116 |

OTHER PUBLICATIONS

Extended European Search Report dated Mar. 14, 2024 for European Patent Application No. 23219300.3.
International Search Report for PCT/KR2021/008924 mailed on Mar. 24, 2022 and its English translation from WIPO (now published as WO 2022/131467).
Written Opinion of the International Searching Authority for PCT/KR2021/008924 mailed on Mar. 24, 2022 and its English translation from WIPO (now published as WO 2022/131467).
Office Action dated Jul. 14, 2022 for Korean Patent Application No. 10-2020-0174276 and its English translation from Global Dossier.
Notice of Allowance dated Jun. 19, 2023 for Korean Patent Application No. 10-2020-0174276 and its English translation from Global Dossier.

* cited by examiner

| CLASS | TYPE1 | TYPE2 | TYPE3 |
|---|---|---|---|
| Setting1 | Sound 5 | Sound 1 | Sound 5 |
| Setting2 | Sound 5 | Vibration 2 | Sound 5 |
| Setting3 | Vibration 5 | Vibration 1 | Vibration 5 |
| Setting4 | Vibration 5 | Sound 2 | Vibration 5 |
| Setting5 | Sound 5 | Sound 1 | Sound 7 |
| Setting6 | Vibration 5 | Vibration 1 | Vibration 7 |

| Sound 1 | Vibration 1 | Light 1 |
|---------|-------------|---------|
| Sound 2 | Vibration 2 | Light 2 |
| Sound 3 | Vibration 3 | Light 3 |
| Sound 4 | Vibration 4 | Light 4 |
| ⋮ | ⋮ | ⋮ |

METHOD FOR GENERATING ALARM ABOUT CONTINUOUS BIOMETRIC INFORMATION

CROSS-REFERENCE TO RELATED APPLICATIONS

The present application is a continuation of U.S. patent application Ser. No. 18/265,432 filed on Jun. 6, 2023, which is the U.S. National Phase of PCT Application No. PCT/KR2021/008924 filed on Jul. 13, 2021, which claims the priority to Korean Patent Application No. 10-2020-0174276 filed on Dec. 14, 2020, the entire contents of which are incorporated herein by reference.

TECHNICAL FIELD

The present invention relates to a method for generating an alarm pertaining to continuous biological data and, more specifically, to an alarm generation method in which, if an alarm condition is satisfied, an alarm is output to a user while maintaining the alarm in an activated state during a set alarm period, and changing the alarm type selected by the user during the alarm period, thereby enabling the user to be made continually aware of the alarm and be prompted to input information or take an action in response to the alarm while not causing inconvenience to the user with frequent alarms; and, when the alarm condition is satisfied, an operating mode of a receiver is determined and the mode of the alarm type, which has been set in accordance with the alarm condition, is changed to an alarm type corresponding to the operating mode of the receiver, thereby making it possible to prevent an alarm from being generated against the user's wishes.

BACKGROUND

Diabetes is a leading cause of death worldwide and is a factor which causes physical impairments, and therefore many people develop health problems due to diabetes. In particular, diabetes is a serious disease which causes heart and kidney disease, blindness, neural damage and high blood pressure. Looking at long-term clinical studies, the occurrence of complications can be significantly reduced by means of adequately controlling blood glucose levels. Therefore, it is important to continuously manage diabetes, and a major factor thereof is self-monitoring of blood glucose levels.

Due to such requirements, personal biometric devices which can directly test the blood glucose of the user are widely supplied to and used by users. Typical blood glucose measuring devices measure a user's blood glucose level by smearing the user's blood onto a sensor strip in the form of a test paper. That is, the sensor strip smeared with blood is inserted into the blood glucose measuring device and the blood glucose level measured via the sensor strip is displayed on the blood glucose measuring device.

At this time, the blood glucose measuring device receives an electrical signal generated by an electrochemical reaction of the collected blood and the reactants inside the sensor strip and so measures the blood glucose level. This kind of blood-collecting blood glucose meter (finger prick method) helps with a diabetes patient's blood glucose management, but there is a problem in that it is difficult to accurately understand the frequently changing blood glucose value since only the result at the time of measurement is indicated.

Diabetes patients generally move between hyperglycaemic and hypoglycaemic states, and with emergencies occurring in the hypoglycaemic state, and when the supply of glucose does not last for a long time, they may lose consciousness or, in the worst case, may lose their lives. Therefore, the immediate detection of a hypoglycaemic state is very important to diabetes patients. But blood-collecting blood glucose meters which intermittently measure blood glucose have obvious limitations.

In order to overcome the limitations of such blood-collecting blood glucose meters, a continuous blood glucose measuring system (Continuous Glucose Monitoring System, CGMS) which is inserted into the body to measure blood glucose at intervals of a few minutes has been developed, and this can be used to manage diabetic patients and easily cope with emergency situations.

The continuous blood glucose measuring system comprises: a body-attachable unit which is inserted into the body and is for collecting test material such as a bodily fluid of the user and measuring the blood glucose; and a receiver for communicating with the body-attachable unit and displaying the blood glucose data measured by the body-attachable unit.

The receiver not only outputs the blood glucose data received from the body-attachable unit to the user, but also can provide an alarm to the user when the user has hyperglycaemia or hypoglycaemia on the basis of the blood glucose data, or can monitor the service condition of the body-attachable unit and provide an alarm to the user.

For example, the receiver monitors the service life of the body-attachable unit and can provide an alarm for replacing the body-attachable unit, or can provide an alarm for requesting calibration of the body-attachable unit.

To be more specific, body-attachable units cannot be permanently used and have a fixed term of life, for example, a service life of 15 days or 1 month, so replacement is necessary when the service life expires. If the service life has ended, the body-attachable unit does not measure the blood glucose in the body after this endpoint, and there are also no more data transmissions to a communication terminal. There are also cases where, in some circumstances, the power source of the body-attachable unit is automatically turned off.

Therefore, since the user cannot receive any more blood glucose data from the body-attachable unit after the service life of the body-attachable unit has ended, the user should be notified to replace the body-attachable unit in advance before the service life of the body-attachable unit ends.

Meanwhile, in order to provide accurate blood glucose data to the user, the blood glucose data received from the body-attachable unit must be initially calibrated using a separate blood glucose measuring device, and thereafter must continue to be calibrated at fixed periods during the service life of the body-attachable unit with a reference blood glucose value measured by a separate blood glucose measuring device. If there is no calibration of the blood glucose value measured by the body-attachable unit, the reliability of the blood glucose value measured by the body-attachable unit falls, and therefore an alarm for periodically calibrating the blood glucose value must be provided to the user.

Thus, the receiver can output various alarms to the user while the body-attachable unit is being used, and if it is an important alarm, the receiver determines whether the user has responded to the alarm by taking a required action or inputting required information, and then if the user has not responded to the alarm, an additional alarm must be provided to the user.

If it is an important alarm, the alarm must be provided to the user until the user takes an action or inputs information in response to the alarm, but there is a problem in that the user comes to feel fatigued from the alarms and may avoid or ignore responding to the alarm as a result of various alarms being provided to the user or repeated additional alarms being provided to the user.

In addition, set alarms are output even when the user is reluctant to inform the people around them of their use of the body-attachable unit or does not want to be disturbed by the alarm during a meeting, so there is the problem of alarms being provided to the user against the user's wishes.

DETAILS OF THE INVENTION

Problem to be Solved

The present invention aims to resolve the problems of the prior art, such as those of continuous blood glucose measuring devices, which continually measure biometric data and provide an alarm from the continuous biometric data, and an object of the present invention is to provide an alarm generation method in which, if an alarm condition is satisfied, an alarm is output to a user while maintaining the alarm in an activated state during a set alarm period, and changing the alarm type during the alarm period.

Another object of the present invention is to provide an alarm generation method in which, when an alarm condition is satisfied, the level of fatigue of and inconvenience to the user due to the alarm can be reduced by maintaining an alarm in an activated state during a set alarm period, and changing the alarm type selected by the user during the alarm period.

Yet another object of the present invention is to provide an alarm generation method in which, when the alarm condition is satisfied, an operating mode of a receiver is determined and the mode of the alarm type, which has been set in accordance with the alarm condition, is changed to an alarm type corresponding to the operating mode of the receiver.

Solution to the Problem

In order to achieve the objects of the present invention, a method for generating an alarm pertaining to continuous biometric data according to the present invention is characterized by comprising steps of: determining whether a set alarm condition is satisfied; if the alarm condition is satisfied, activating an alarm for a set alarm period and generating a first type of alarm and outputting same to a user; in the activated alarm period, continuing on from the first type of alarm, generating a second type of alarm that is different from the first type and outputting same to the user; and after the alarm period has elapsed, continuing on from the second type of alarm, generating a third type of alarm and outputting same to the user.

The alarm generation method according to the present invention is characterized in that the first type of alarm is continuously generated during a set first time in the alarm period, and the second type of alarm is generated during the remaining alarm period after the first time has elapsed.

The alarm generation method according to one embodiment of the present invention is characterized in that the first type of alarm is continuously generated until a user command is input during the alarm period, and the second type of alarm is generated during the remaining alarm period after the user command is input. The alarm generation method is characterized in that, in the alarm generation method according to another embodiment of the present invention, the third type of alarm is the same as the first type of alarm.

Preferably, the alarm generation method according to the present invention is characterized in that in generating the second type of alarm, the intensity or frequency of the second type of alarm is adjusted to be inversely proportional to the number of inputs of an adjustment user command that is input after the second type of alarm has been generated.

Here, the present invention is characterized in that the first type of alarm, the second type of alarm or the third type of alarm is set as an alarm type selected by the user.

Here, the present invention is characterized in that an interface screen on which the intensity or frequency of the second type of alarm can be set is activated so that the intensity or frequency of the second type of alarm can be set within a range smaller than that of the first type of alarm or the third type of alarm.

Preferably, the alarm generation method according to the present invention is characterized by further comprising a step of determining a mode of a receiver, and the first type of alarm, the second type of alarm or the third type of alarm is generated in the same mode as the determined mode of the receiver.

The alarm generation method according to the present invention is characterized in that the third type of alarm is the same as the first type of alarm in the same mode as the mode of the receiver.

The alarm generation method according to the present invention is characterized in that the continuous biometric data is a user's blood glucose data which is measured by a continuous blood glucose measuring device attached to the user's body, and the alarm condition is whether an input period for calibration data has arrived.

The alarm generation method according to the present invention is characterized in that the continuous biometric data is a user's blood glucose data which is measured by a continuous blood glucose measuring device attached to the user's body, and the alarm condition is whether the time to replace the continuous blood glucose measuring device has arrived.

Advantages of the Invention

The method for generating an alarm pertaining to continuous biometric data according to the present invention has advantages such as the following.

Firstly, in the method for generating an alarm pertaining to continuous biometric data according to the present invention, if an alarm condition is satisfied, an alarm is output to a user while maintaining the alarm in an activated state during a set alarm period, and changing the alarm type selected by the user during the alarm period, thereby making it possible to prompt the user to input information or take an action in response to the alarm without ignoring the alarm, while not causing inconvenience to the user due to frequent alarms.

Secondly, in the method for generating an alarm pertaining to continuous biometric data according to the present invention, when the alarm condition is satisfied, an operating mode of a receiver is determined and the alarm type, which has been set in accordance with the alarm condition, is changed to an alarm type corresponding to the operating mode of the receiver, thereby making it possible to prevent an alarm from being generated against the user's wishes.

SPECIFIC DETAILS FOR IMPLEMENTING THE INVENTION

It should be noted that the technical terms used in the present invention are merely used to describe a specific embodiment of the invention, and are not intended to limit the present invention. Furthermore, the technical terms used in the present invention should be interpreted as having the meaning commonly understood by a person skilled in the art to which the present invention belongs unless specifically defined otherwise in the present invention, and should not be interpreted as having an excessively inclusive meaning or an excessively limited meaning. Furthermore, when a technical term used in the present invention is an erroneous technical term that fails to accurately express a concept of the present invention, it should be understood as having been replaced by a technical term that can be correctly understood by those skilled in the art.

Furthermore, expressions in the singular used in the present invention include expressions in the plural unless clearly intended otherwise in context. In the present invention, terms such as "consisting of" or "comprising" should not necessarily be interpreted as including all the constituent elements or steps described in the invention, and some constituent elements or some steps may not be included, or additional constituent elements or steps may be further included.

Furthermore, it should be noted that the accompanying drawings are merely to facilitate the understanding of the concept of the present invention, and the concept of the present invention should not be construed as being limited by the accompanying drawings.

Hereinbelow, the method for providing an alarm pertaining to continuous biometric data according to the present invention is described with reference to the accompanying drawings.

Figure 1:
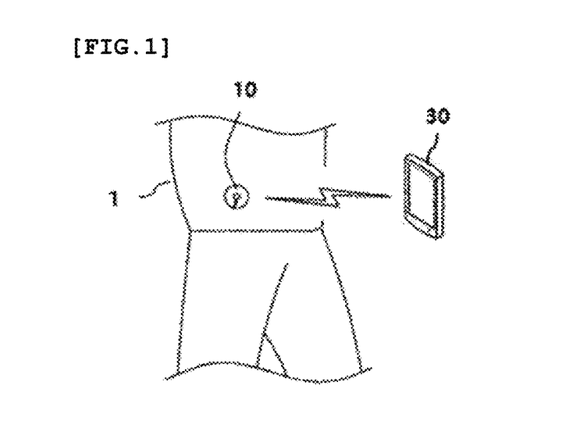
FIG. 1 is a drawing for describing a continuous biometric data measuring system according to the present invention.

FIG. 1 is a drawing for describing a continuous biometric data measuring system according to the present invention.

Referring to FIG. 1, a continuous biometric data measuring system according to one embodiment of the present invention comprises a body-attachable unit (10) and a receiver (30).

The body-attachable unit (10) is attached to a body (1), and, when the body-attachable unit (10) is attached to the body, one end of a sensor of the body-attachable unit (10) is inserted into the skin to periodically extract a bodily fluid of the body to continuously measure biometric data such as blood glucose. Here, the body-attachable unit (10) comprises the sensor which is inserted into the skin to extract the bodily fluid, and a transmitter which transmits the biometric data to the receiver (30) after measuring the biometric data from the bodily fluid. The sensor and transmitter are assembled together at a factory to manufacture the body-attachable unit, and the body-attachable unit (10) is further mounted on an applicator (not depicted) which attaches the body-attachable unit (10) to the body.

The user removes the applicator from its wrapping and then positions the applicator on the area of the body where the body-attachable unit is to be fitted, and then places the body-attachable unit on the skin using the applicator.

After placement of the body-attachable unit (10) on the skin is completed, the body-attachable unit (10) and the receiver (30) are connected in communication with each other so that the biometric data measured by the body-attachable unit (10) is transmitted and received.

Here, the receiver (30) can establish communication with the body-attachable unit (10), and it is possible to use a dedicated terminal or smartphone or the like which can receive biometric data from the body-attachable unit (10) and provide the biometric data to a user. The receiver is not limited to smartphones, tablet PCs or notebooks, and the type of terminal does not matter as long as the terminal includes a communication function and a program or application can be installed.

The receiver (30) periodically receives biometric data from the body-attachable unit (10) after being connected in communication with the body-attachable unit (10), and calibrates the received biometric data and outputs the generated biometric data to the user.

The receiver (30) provides an alarm to the user on the basis of the service condition of the body-attachable unit (10) or provides an alarm to the user on the basis of the biometric data received from the body-attachable unit (10).

For example, the receiver (30) provides a danger alarm to the user on the basis of the biometric data received from the body-attachable unit (10) when the biometric data exceeds a set value, or provides a replacement alarm to the user when the time is arriving for replacing a body-attachable unit (10) which has a limited service life, or provides a calibration alarm to the user when the time is arriving for inputting calibration information for the biometric data measured via the body-attachable unit (10).

Various pieces of the user's biometric data can be continuously measured via the body-attachable unit (10), but blood glucose data is described hereinbelow as an example of biometric data.

Figure 2:
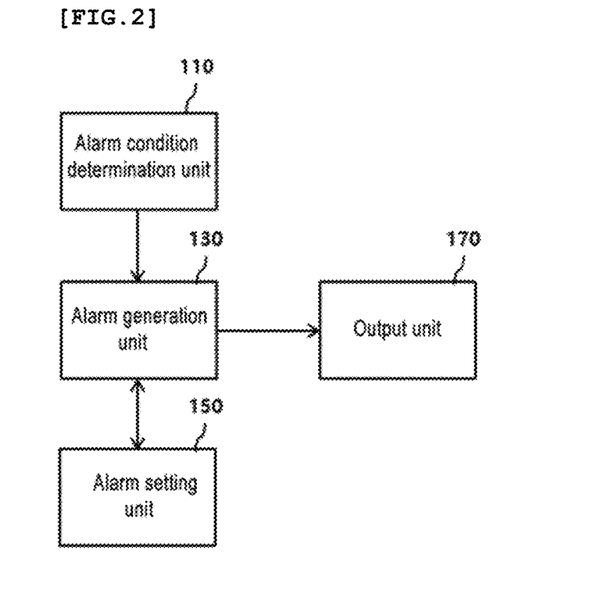
FIG. 2 is a function block diagram for describing a device which provides an alarm pertaining to continuous blood glucose data according to the present invention.

FIG. 2 is a function block diagram for describing a device which provides an alarm pertaining to continuous blood glucose data according to the present invention.

More specifically, referring to FIG. 2, an alarm condition determination unit (110) determines whether an alarm triggering condition is satisfied on the basis of blood glucose data measured by the body-attachable unit or the service condition of the body-attachable unit, or determines whether an alarm clearing condition is satisfied on the basis of a user command input via the receiver or the service condition of the body-attachable unit.

When an alarm triggering condition is satisfied, an alarm generation unit (130) generates an alarm signal by activating and maintaining an alarm during an alarm period and in this state, changing the alarm type to a set alarm type depending on an inputted user input or depending on the time elapsed in the alarm period. An alarm setting unit (150) sets the alarm type for the alarm period for each kind of alarm depending on a user command input via a user interface unit (not shown), and stores information pertaining to the alarm type for the alarm period for each kind of set alarm.

An output unit (170) outputs to the user the various types of alarm which have been continuously generated in the alarm generation unit (130) during the alarm period. Here, the output unit (170) may use a speaker or a display, and the output unit (170) can output an audio alarm to the user via the speaker or can output a visual alarm to the user via the display.

Meanwhile, the alarm generation unit (130) enacts control so that an alarm is not output to the user after the activation of the alarm has ended when the alarm clearing condition is satisfied.

Here, there may be differences in the various kinds of alarms set by the user or the manufacturer of the body-attachable unit and in the alarm triggering conditions for each alarm. For example: an alarm triggering condition is satisfied if the body-attachable unit has a limited service life and the replacement period for the body-attachable unit is arriving within a set time; an alarm triggering condition is satisfied if the blood glucose value measured by the body-attachable unit exceeds a set threshold blood glucose value; and an alarm triggering condition is satisfied if the calibration period of the body-attachable unit is arriving within a set time.

Meanwhile, by way of example of the alarm clearing conditions: an alarm clearing condition is satisfied if the body-attachable unit is replaced with a new body-attachable unit when the replacement period for the body-attachable unit arrives; an alarm clearing condition is satisfied if the user eats a meal or administers insulin or the like after the blood glucose value measured by the body-attachable unit has exceeded the set threshold blood glucose value; and an alarm clearing condition is satisfied if a calibration period of the body-attachable unit arrives and the user inputs information about a reference blood glucose value measured by a blood glucose measuring device.

Figure 3:
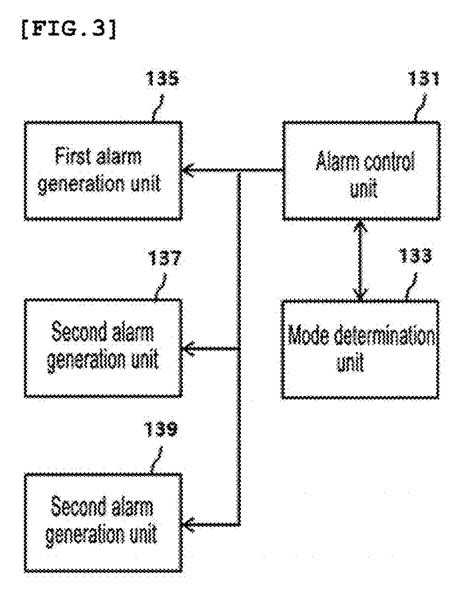
FIG. 3 is a function block diagram for describing an example of an alarm generation unit according to the present invention.

When an alarm triggering condition is satisfied, the alarm generation unit according to the present invention maintains an activated alarm state during a set alarm period, and changes the alarm type during the alarm period, and outputs the alarm to the user. FIG. 3 is a function block diagram for describing an example of an alarm generation unit according to the present invention.

More specifically referring to FIG. 3, when a set alarm triggering condition is satisfied, an alarm control unit (131) determines the alarm period, the combination of alarm types and the generation conditions for each alarm type that is dependent on the kind of alarm and generates an alarm triggering signal in accordance with the determined combination of alarm types and generation conditions during the alarm period. The alarm control unit (131) enacts control so that the activated alarm state is maintained during the alarm period that is dependent on the kind of alarm and provides continuous alarms of different types to the user.

The combination of alarm types that is dependent on the kind of alarm comprises a first type of alarm, a second type of alarm and a third type of alarm, although the combination of alarm types can comprise a different number of alarm types depending on the field in which the present invention is applied.

Meanwhile, it is possible to set different alarm start conditions and alarm stop conditions for the first type of alarm, second type of alarm and third type of alarm which constitute the combination of alarm types that is dependent on the kind of alarm.

The alarm control unit (131) generates a first alarm triggering signal which is set to trigger the first type of alarm in accordance with the generation condition for the first type of alarm, a second alarm triggering signal which is set to continue on from the first type of alarm and trigger the second type of alarm in accordance with the generation condition for the second type of alarm, and a third alarm triggering signal which is set to continue on from the second type of alarm and trigger the third type of alarm in accordance with the generation condition for the third type of alarm.

When a first alarm generation unit (135) receives the first alarm triggering signal from the alarm control unit (131), said first alarm generation unit generates the first type of alarm in accordance with the first alarm triggering signal and outputs the generated first type of alarm to the user via the output unit.

When the second alarm generation unit (137) receives the second alarm triggering signal from the alarm control unit (131), said second alarm generation unit generates the second type of alarm in accordance with the second alarm triggering signal and outputs the generated second type of alarm to the user via the output unit.

When the third alarm generation unit (137) receives the third alarm triggering signal from the alarm control unit (131), said third alarm generation unit generates the third type of alarm in accordance with the third alarm triggering signal and outputs the generated third type of alarm to the user via the output unit.

Preferably, the alarm generation unit can further comprise a mode determination unit (133), and the mode determination unit (133) determines the operating mode of the receiver at the time points at which the first type of alarm, second type of alarm and third type of alarm occur. The alarm control unit (131) synchronizes with the operating mode of the receiver at the time points at which the first type of alarm, second type of alarm and third type of alarm occur and changes the preset modes of the first type of alarm, second type of alarm and third type of alarm to be the same as the operating mode of the receiver, and generates the first alarm triggering signal, second alarm triggering signal and third alarm triggering signal so that the first type of alarm, second type of alarm, and third type of alarm are triggered in the same mode as the operating mode of the receiver.

Figure 4:
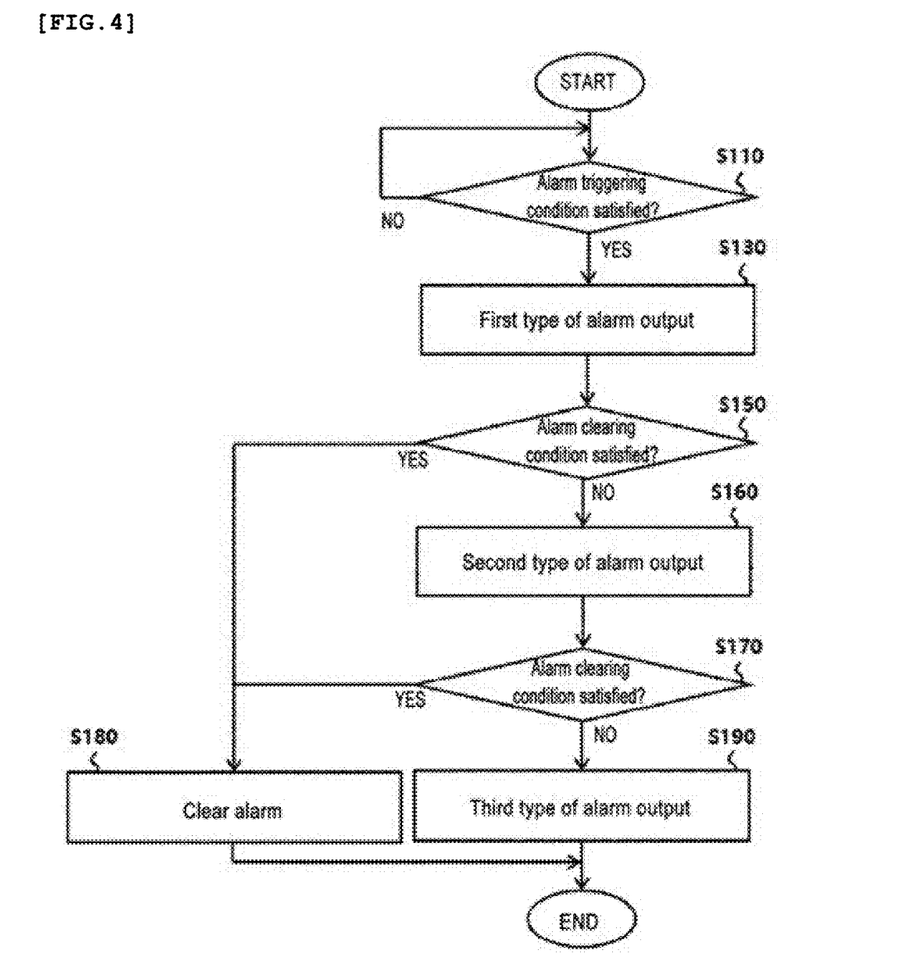
FIG. 4 is a flow diagram for describing a method for generating an alarm pertaining to continuous biometric data according to the present invention.

FIG. 4 is a flow diagram for describing a method for generating an alarm pertaining to continuous biometric data according to the present invention.

More specifically referring to FIG. 4, it is determined whether an alarm triggering condition is satisfied (S110).

When the alarm triggering condition is satisfied, the generation condition for each alarm period, combination of alarm type, and alarm type that is dependent on the kind of alarm is determined, and, firstly, in the combination of alarm types, the alarm type and generation condition of the first type of alarm are determined and a first alarm triggering signal is generated and then the first type of alarm is generated in accordance with the first alarm triggering signal and output to the user (S130). Here, the generation condition of the first type of alarm may be a generation start condition of the first type of alarm and a generation end condition of the first type of alarm. For example, the generation of the first type of alarm is started in accordance with the first alarm triggering signal and is output to the user, and the generation of the first type of alarm is ended after the set time has elapsed or when an alarm change command is received from the user.

It is determined whether an alarm clearing condition is satisfied while the first type of alarm is being output to the user (S150).

If the alarm clearing condition is satisfied, the activation of the alarm is immediately cancelled to prevent the alarm from continuing to be output to the user (S180).

However, if it is determined that the alarm clearing condition could not be satisfied even after outputting the first type of alarm to the user, in the combination of alarm types, the alarm type and generation condition of the second type of alarm are determined and a second alarm triggering signal is generated and then the second type of alarm is generated in accordance with the second alarm triggering signal and output to the user (S160).

It is determined whether an alarm clearing condition is satisfied while the second type of alarm is being output to the user (S170).

When the alarm clearing condition is satisfied, the activation of the alarm is immediately cancelled to prevent the alarm from continuing to be output to the user (S180).

However, when it is determined that the alarm clearing condition could not be satisfied even after outputting the second type of alarm to the user, in a combination of alarm types, the alarm type and generation condition of the third type of alarm are determined and a third alarm triggering signal is generated and then the third type of alarm is generated in accordance with the third alarm triggering signal and output to the user (S190).

Figure 5:
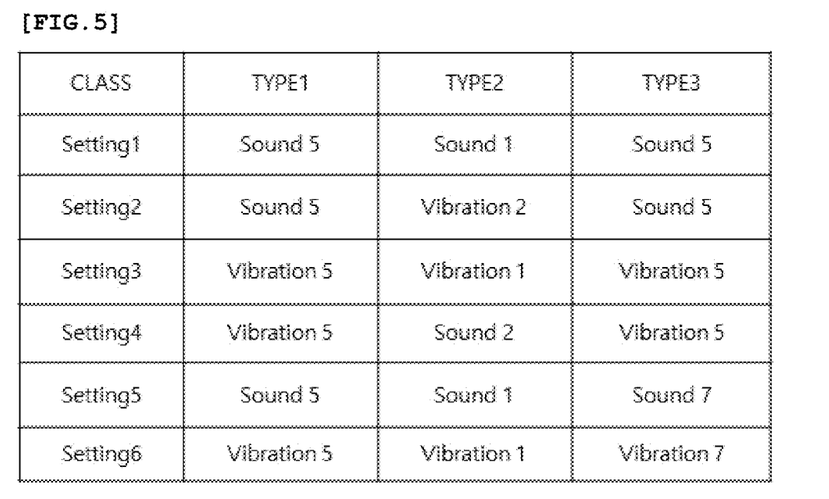
FIG. 5 depicts an example of a combination of alarm types that are set in the present invention.

FIG. 5 depicts an example of a combination of alarm types set by the present invention.

As depicted in FIG. 5, when the combination of alarm types comprises three alarm types, setting 1 may be a combination of (sound 5, sound 1, sound 5), setting 2 may be a combination of (sound 5, vibration 2, sound 5), setting 3 may be a combination of (vibration 5, vibration 1, vibration 5), setting 4 may be a combination of (vibration 5, sound 2, vibration 5), setting 5 may be a combination of (sound 5, sound 1, sound 7), and setting 6 may be a combination of (vibration 5, vibration 1, vibration 7).

Here, settings 1 to 6 may be preset by the manufacturer or the three alarm types constituting the combination of alarm types can be set as the user chooses.

The modes of the three alarm types constituting the combination of alarm types may be set as sounds, vibrations, lights, or the like, and the intensity or frequency can be set to be different in accordance with the alarm type for each sound, vibration and light.

Figure 6:
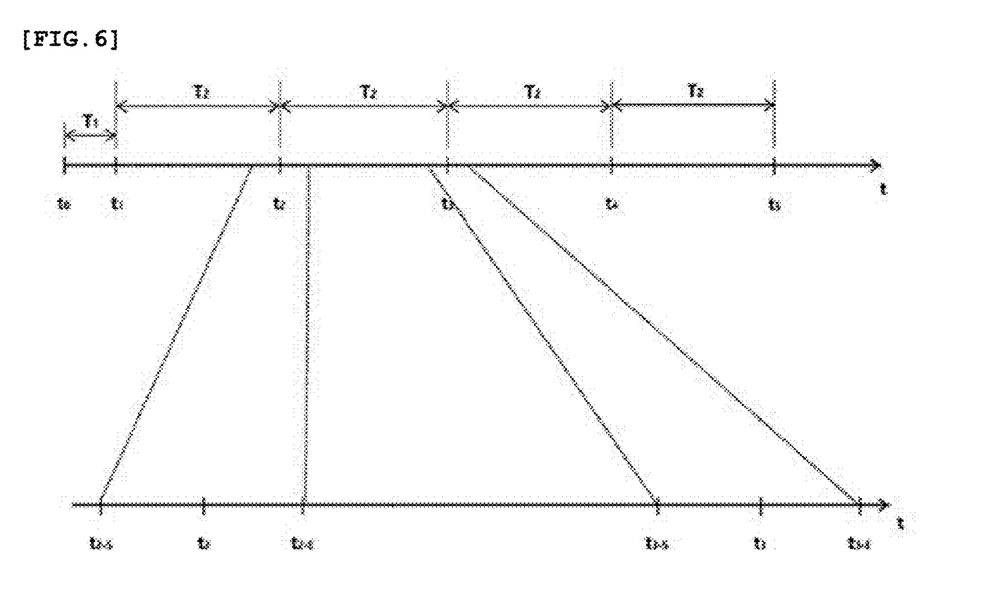
FIG. 6 is a drawing for describing the alarm trigger timings when the alarm triggering condition is the arrival of a calibration period.

FIG. 6 is a drawing for describing alarm trigger timings when an alarm triggering condition is the arrival of a calibration period.

When the user's blood glucose is continuously measured via the body-attachable unit, the blood glucose value measured by the body-attachable unit should be periodically calibrated with a reference blood glucose value measured with a test strip and blood glucose measuring device so that accurate blood glucose values can be obtained.

After attaching the body-attachable unit to the body, a stabilization step is carried out during set time ($T_1$), and, after the stabilization, a reference blood glucose value is input for each calibration period ($T_2$) to calibrate the blood glucose value measured by the body-attachable unit.

When a first calibration period ($t_2$) arrives, a calibration alarm is generated in the alarm period ($t_{2-S}$ to $t_{2-E}$), which is set with respect to the first calibration period ($t_2$), and the alarm is provided to the user.

Also, when a second calibration period ($t_3$) arrives, a calibration alarm is generated in the alarm period ($t_{3-S}$ to $t_{3-E}$), which is set with respect to the second calibration period ($t_3$), and is provided to the user. Thus, until the service life of the body-attachable unit expires, calibration alarms continue to be generated and output to the user when a calibration period arrives.

Figure 7:
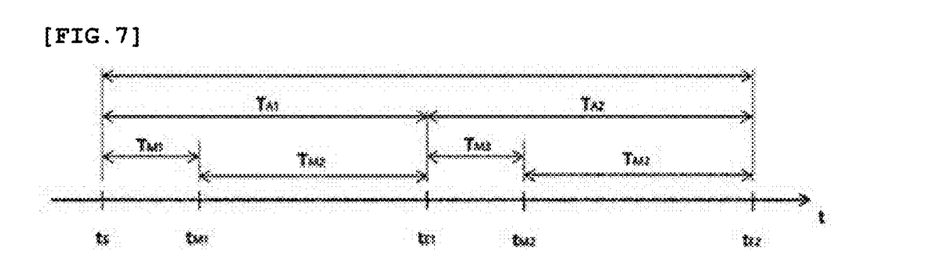
FIG. 7 is a drawing for describing an example in which a calibration alarm is provided to the user as a combination of various alarm types during an alarm period.

FIG. 7 is a drawing for describing an example in which a calibration alarm is provided to the user as a combination of various alarm types during an alarm period.

Referring to FIG. 7, a calibration alarm period ($T_{AT}$) is split into a plurality of detailed alarm periods ($T_{A1}$, $T_{A2}$), and when the calibration alarm period arrives, a first type of alarm is continually output to the user during a first time ($T_{M1}$) which has been set in accordance with the generation condition for the first type of alarm in a first detailed alarm period ($T_{A1}$). During the output of the first type of alarm to the user, the alarm is cleared if an alarm clearing condition is input, i.e., calibration information, by the user.

However, if calibration information is not input even after the first type of alarm has been continually output to the user, or if an alarm change command is received from the user after the first type of alarm has been output to the user, a second type of alarm is continually output to the user during a second time ($T_{M2}$) which has been set in accordance with the generation condition for the second type of alarm in the first detailed alarm period ($T_{A1}$).

During output of the second type of alarm to the user, the alarm is cleared if calibration information is input by the user. However, if calibration information is not input by the user before the first detailed alarm period ends, a third type of alarm is continually output to the user during a third time ($T_{M3}$) which has been set in accordance with the generation condition for the third type of alarm in the second detailed alarm period ($T_{A2}$). If calibration information is not input even after the third type of alarm has been continually output to the user, or if an alarm change command is received from the user after the third type of alarm has been output to the user, the second type of alarm is continually output to the user during a second time ($T_{M2}$) which has been set in accordance with the generation condition for the second type of alarm in the second detailed alarm period ($T_{A2}$).

Preferably, the intensity or frequency of the second type of alarm can be set within a smaller range than that of the first type of alarm or the third type of alarm. Therefore, by accurately delivering the calibration alarm to the user with the first type of alarm and then changing to a second type of alarm with a lower intensity or frequency than the first type of alarm, the level of fatigue of the user due to the frequent alarms can be reduced but nevertheless at the same time the user can be prompted to continue to input calibration information. Meanwhile, if the user also does not input calibration information during the second type of alarm, the alarm is changed again to a third type of alarm having a higher intensity or frequency than the second type of alarm and is provided to the user, thereby a calibration alarm can be accurately delivered to the user once again.

Preferably, the intensity or frequency of the third type of alarm can be set to be larger than that of the first type of alarm. Therefore, if calibration information is not input despite the first type of alarm and second type of alarm, it is possible to prompt the input of calibration information before the calibration period ends.

Figure 8:
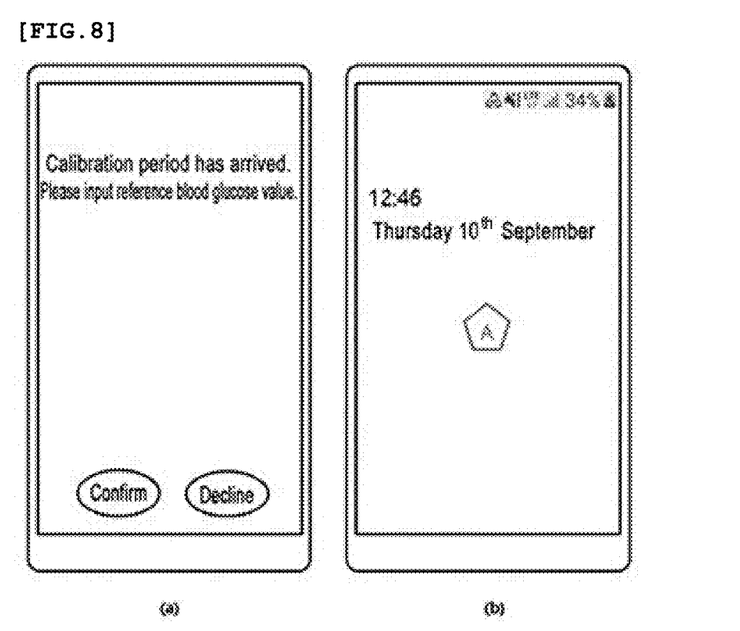
FIG. 8 depicts an example of a user interface for providing a calibration alarm according to the present invention.

FIG. 8 depicts an example of a user interface for providing a calibration alarm according to the present invention.

As depicted in FIG. 8(a), when a calibration period arrives, a display unit is activated with a user interface screen having a message, which notifies that the calibration period has arrived, together with the first type of alarm. If the 'Confirm' button is clicked, a user interface screen for input of calibration information is activated so that the user can input calibration information.

However, as depicted in FIG. 8(b), if the user clicks the 'Decline' button, the display unit is activated with a user interface screen having an icon, which requests input of calibration information, together with the second type of alarm.

Figure 9:
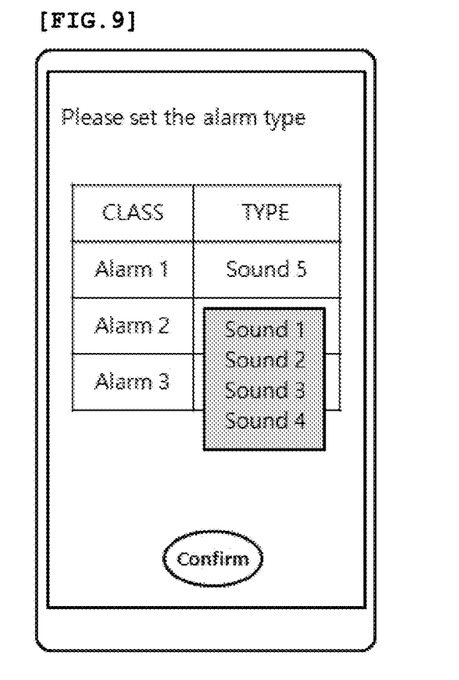
FIG. 9 is a drawing for describing an example of a user interface screen for setting the alarm type.

FIG. 9 is a drawing for describing an example of a user interface screen for setting the alarm type.

As depicted in FIG. 9, the user can set a combination of alarm types by selecting the first type of alarm, second type of alarm, third type of alarm for each kind of alarm. Preferably, the user interface is activated so that the intensity or frequency of the second type of alarm can be selected only within a range smaller than that of the first type of alarm, and the user interface is activated so that the intensity or frequency of the third type of alarm can be selected only within a range the same as or larger than that of the first type of alarm.

Figure 10:
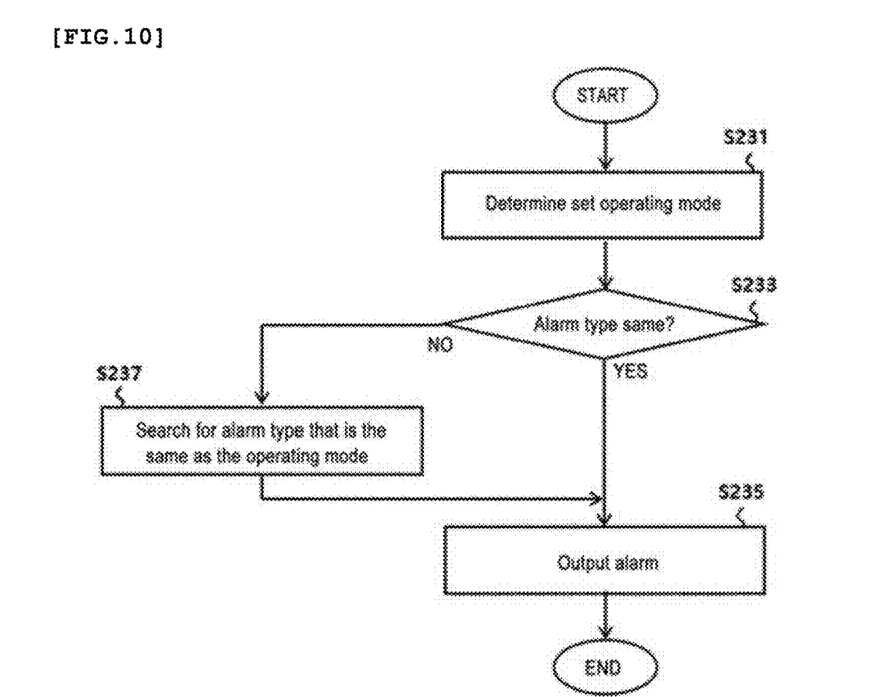
FIG. 10 is a flow diagram for describing an example of a method for changing the mode of the alarm type in synchronization with an operating mode of a receiver.

FIG. 10 is a flow diagram for describing an example of a method for changing the mode of the alarm type in synchronization with an operating mode of a receiver.

When the alarm triggering condition is satisfied, the set operating mode of the receiver is determined (S231).

In the combination of alarm types, it is determined if the operating mode of the first type of alarm is the same as the operating mode of the receiver (S233).

When the operating mode of the first type of alarm is the same as the operating mode of the receiver, a first alarm is generated as the preset first type of alarm and output to the user (S235).

However, when the operating mode of the first type of alarm and the operating mode of the receiver are different from each other, the operating mode of the preset first type of alarm is changed to be the same as the operating mode of the receiver and the first alarm is generated and the generated first alarm is output to the user (S237).

In the same manner, when generating the second type of alarm or the third type of alarm, it is determined whether the operating mode of the receiver and the preset operating mode of the second type of alarm or the third type of alarm are the same as each other, and the operating mode of the second type of alarm or third type of alarm and the operating mode of the receiver are synchronized with each other to generate a second alarm or a third alarm.

Thus, when the alarm condition is satisfied, the operating mode of the receiver is determined and the operating mode of the alarm type which has been set in accordance with the alarm condition is changed to an alarm type corresponding to the operating mode of the receiver, thereby enabling the generation of an alarm against the user's wishes to be prevented.

Figure 11:
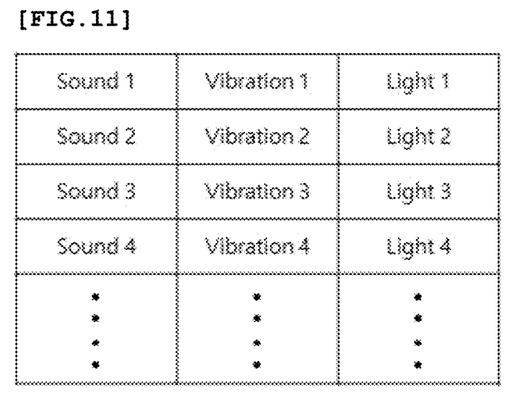
FIG. 11 depicts an example of a mapping table for the alarm types of the different operating modes.

FIG. 11 depicts an example of a mapping table for the alarm types of the different operating modes.

As depicted in FIG. 11, when changing the operating mode of the alarm type to an operating mode that is the same as the operating mode of the receiver, the alarm type is changed on the basis of a mapping table.

For example, in the mapping table, alarm type sound 4, alarm type vibration 4 and alarm type light 4 are mapped to each other. The combination of alarm types for the calibration alarm is sound 4, sound 1, sound 4, and when the operating mode of the receiver is set to vibration mode, the first type of alarm changes to vibration 4 which is mapped to sound 4 and the first type of alarm is generated.

Meanwhile, the embodiments of the present invention described above may be written as a computer-executable program and may be implemented in a general-purpose digital computer that operates the program using a computer-readable recording medium.

Computer-readable recording media include storage media such as magnetic storage media (e.g., ROM, floppy disk, hard disk, etc.), optical reading media (e.g., CD-ROM, DVD, etc.), and carrier waves (e.g., transmission over the Internet).

The present invention has been described with reference to the embodiments depicted in the drawings, but the embodiments are merely examples, and it should be understood by those skilled in the art that various modifications and other equivalent embodiments based thereon are possible. Therefore, the true technical scope of protection for the present invention should be determined by the technical concepts in the accompanying registered claims.

What is claimed is:

1. A method for providing an alarm related to continuous biometric information, the method comprising:
    determining whether a set alarm condition is satisfied; and
    when the alarm condition is satisfied, determining an operation mode of a receiver, wherein an alarm mode set according to the alarm condition depends from the operation mode of the receiver;
    determining whether the alarm mode set according to the alarm condition and the operation mode of the receiver are the same as each other; and
    providing the alarm by synchronizing the alarm mode set according to the alarm condition with the operation mode of the receiver,
    wherein when the alarm mode set and the operation mode of the receiver are not the same as each other, the providing of the alarm comprises changing an alarm mode to be the same as the operating mode of the receiver based on a mapping table regarding a plurality of alarm modes.

2. The method for providing the alarm according to claim 1, further comprising
    when the alarm condition is satisfied, sequentially generating the alarm with the alarm mode set according to the alarm condition for a set alarm period,
    wherein when generating the alarm, the alarm is generated by being synchronized to the operation mode of the receiver.

3. The method for providing the alarm according to claim 2,
    an alarm type of the alarm mode set according to the alarm condition is synchronized to an alarm type of the operation mode of the receiver mapped to an alarm type of the alarm mode, stored in a mapping table.

4. The method for providing the alarm according to claim 3, wherein:

when the alarm condition is satisfied, a first type alarm, a second type alarm, and a third type alarm are generated sequentially as the set alarm mode for the set alarm period, and when the first type alarm, the second type alarm, and the third type alarm are generated, the alarm is generated by being synchronized to the operation mode of the receiver.

5. The method for providing the alarm according to claim 4, wherein the first type alarm and the second type alarm are different from each other, and the second type alarm and the third type alarm are different from each other.

6. The method for providing the alarm according to claim 4, wherein the second type alarm is generated by adjusting an intensity or a frequency of the second type alarm to be inversely proportional to a number of inputs of an adjustment user command inputted after the second type alarm is generated.

7. The method for providing the alarm according to claim 4, wherein the intensity or the frequency of the second type alarm is set to a range lower than the first type alarm or the third type alarm.

8. The method for providing the alarm according to claim 4, wherein an intensity or a frequency of the third type alarm is set to a range higher than the first type alarm.

9. The method for providing the alarm according to claim 1, wherein the continuous biometric information is blood glucose information of a user measured through a continuous blood glucose measurement device attached to a body of the user.

* * * * *